US009873925B2

(12) United States Patent
Shimomura et al.

(10) Patent No.: US 9,873,925 B2
(45) Date of Patent: Jan. 23, 2018

(54) METHOD OF RECOVERING HEAVY METAL AND REAGENT FOR RECOVERY OF HEAVY METAL FOR USE IN THE SAME

(71) Applicant: ARKRAY, Inc., Kyoto (JP)

(72) Inventors: Yuka Shimomura, Kyoto (JP); Hideko Kosaka, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 615 days.

(21) Appl. No.: 13/622,745

(22) Filed: Sep. 19, 2012

(65) Prior Publication Data
US 2013/0078726 A1 Mar. 28, 2013

Related U.S. Application Data

(60) Provisional application No. 61/538,748, filed on Sep. 23, 2011.

(30) Foreign Application Priority Data

Sep. 22, 2011 (JP) ................... 2011-207905
Aug. 21, 2012 (JP) ................... 2012-182467

(51) Int. Cl.
G01N 33/20 (2006.01)
B01D 17/00 (2006.01)
C22B 7/00 (2006.01)
C22B 3/44 (2006.01)
G01N 31/22 (2006.01)
G01N 33/84 (2006.01)

(52) U.S. Cl.
CPC ............... C22B 7/006 (2013.01); C22B 3/44 (2013.01); G01N 31/22 (2013.01); G01N 33/84 (2013.01); Y02P 10/234 (2015.11)

(58) Field of Classification Search
CPC ........ G01N 33/20; G01N 33/84; G01N 31/22; B01D 17/00
USPC ............................................. 436/74, 80, 81
See application file for complete search history.

(56) References Cited

U.S. PATENT DOCUMENTS

| 4,876,068 | A | 10/1989 | Castaneda |
| 4,920,057 | A | 4/1990 | Castaneda |
| 2006/0154376 | A1 | 7/2006 | Whalen |
| 2010/0120057 | A1* | 5/2010 | Mehra et al. ........... 435/7.1 |
| 2011/0020943 | A1* | 1/2011 | Okamoto et al. ......... 436/73 |

FOREIGN PATENT DOCUMENTS

| CN | 101978263 A | 2/2011 |
| EP | 0319615 B2 | 6/1989 |
| EP | 0536059 A2 | 4/1993 |
| EP | 0536059 * | 7/1993 |
| JP | 58-049490 A | 3/1983 |
| JP | 63-067529 B2 | 12/1988 |
| JP | 02-034655 B2 | 8/1990 |
| JP | 2969226 B2 | 5/1992 |
| JP | 5-232028 A | 9/1993 |
| JP | 2569157 B2 | 1/1997 |
| JP | 09-047768 A | 2/1997 |
| JP | 10-113677 A | 5/1998 |
| JP | 11-042469 A | 2/1999 |
| JP | 2000-136371 A | 5/2000 |
| JP | 2002-316002 A | 10/2002 |
| JP | 2003-194798 A | 7/2003 |
| JP | 2003-235600 A | 8/2003 |
| JP | 2009-294024 A | 12/2009 |
| JP | 2009-294060 A | 12/2009 |
| WO | 2009/012288 A2 | 1/2009 |
| WO | 2009/116669 A1 | 9/2009 |

OTHER PUBLICATIONS

Screening for Mercury in Aqueous Environmental Samples and Urine Samples Using Thin Layer Chromatography Rakhi Agarwal and Jai raj Behari Water Environment Research, vol. 79, No. 12, Nov. 2007.*
Screening for Mercury in Aqueous Environmental Samples and Urine Samples Using Thin Layer Chromatography Water Environment Research, vol. 79, No. 12 Rakhi Agarwal, Jai Raj Behari.*
Extended European Search Report issued in corresponding European Patent Application No. 12185503.5 dated Feb. 27, 2013.
Griffin et al., "Physicochemical Properties of the Native, Zinc- and Manganese-Prepared Metalloprotease of Bacillus polymyxa," Applied Microbiology, 26: 191-195 (1973).
Andoh et al., "Solid Phase Extraction of Ni and Cd by Chelating Cellulose Functionalized with Thiolactic Acid," Bunseki Kagaku, 57: 1027-1032 (2008).
Hayashi et al., "Study on Quantitative Analysis of Heavy Metals in Waste Water by Chelating resin disk preconcentration/ICP-AES," Annual Report of the Kawasaki Municipal Research Institute for Environmental Protection, 45-50 (2003).
Itoh et al., "Determination of Trace Metals in Coastal Seawater around Okinawa and Its Multielement Profiling Analysis," Bunseki Kagaku, 58: 257-263 (2009).
Matsunaga, "Recognition, separation and concentration of metal ions with chelating resins or chelating reagent impregnated resins," Bunseki Kagaku, 50: 89-106 (2000).

(Continued)

Primary Examiner — Krishnan S Menon
Assistant Examiner — Dwan A Gerido
(74) Attorney, Agent, or Firm — Morgan, Lewis & Bockius LLP

(57) ABSTRACT

The present invention provides a method of recovering a heavy metal by which the variation in heavy metal recovery rate among samples can be suppressed. A mixture of a sample and a chelating agent capable of chelating with a heavy metal is prepared. A complex between a heavy metal being in the sample and the chelating agent is formed in the presence of a masking agent for a thiol group in the mixture. The heavy metal in the sample is recovered by recovering the complex. By this method, a heavy metal can be recovered with suppressing the variation in the recovery rate among samples. The chelating agent preferably is 1,5-diphenyl-3-thiocarbazone (dithizone). As the masking agent, N-ethylmaleimide, iodoacetamide, iodoacetic acid, or the like can be used.

13 Claims, No Drawings

(56) References Cited

OTHER PUBLICATIONS

Nagai et al., "The precipitation chromatography of several metal cations with thiooxine impregnated filter paper," Bunseki Kagaku, 24: 184-187 (1975).

Oikawa et al., "Preconcentration of Heavy Metal Ions with Thermo-Sensitive Chitosan and Atomic Absorption Spectrometric Determination of Trace Cadmium in Water," Bunseki Kagaku, 56: 721-728 (2007).

Sakamoto et al., "Pretreatment Method for Determination of Trace Elements in Seawater Using Solid Phase Extraction Column Packed with Polyamino-Polycarboxylic Acid Type Chelating Resin," Bunseki Kagaku, 55: 133-139 (2006).

Shamsipur et al., "Solid phase extraction and determination of sub-ppb levels of hazardous Hg2+ions," Journal of Hazardous Materials B117, 129-133 (2005).

Takeuchi et al., "An Accurate and Rapid Analysis for Lead in Urine Using Solid Phase Extraction Column Packed with a Functional Chelating Resin," Japanese Journal of Occupational Medicine and Traumatology, 55: 15-19 (2007).

Ueno et al., "Bismuthiol II," Handbook of Organic Analytical Reagents, CRC Press, 479-485 (1992).

Ueno et al., "Dithizone and Related Reagents," Handbook of Organic Analytical Reagents, CRC Press, 431-443 (1992).

Ueno et al., "Thiothenoyltrifluoroacetone," Handbook of Organic Analytical Reagents, CRC Press, 487-492 (1992).

Ueno et al., "Thioxine," Handbook of Organic Analytical Reagents, CRC Press, 445-456 (1992).

Watanabe et al., "Spectrophotometric Determination of Small Amounts of Cadmium(II) Using Formation of Zinc(II) Complex with Anionic Porphyrin as an Indicator Reaction," Bunseki Kagaku, 59: 589-595 (2010).

Yamada et al., "Simultaneous determinations of Cu, Cd and Pb in river-water samples by multielement isotope dilution/ICP-MS with the aid of chelating resin preconcentration," Bunseki Kagaku, 50: 433-439 (2001).

Yamamoto et al., "Highly Efficient and Automatic Collection/Concentration with Chelating Resin for Inductively Coupled Plasma Atomic Emission Spectroscopy," Bunseki Kagaku, 55: 715-720 (2006).

Yokoyama et al., "Determination of Aluminum in Water Samples by Flame AAS after Extraction of 8-quinolinol Complex with Nitrobenzene," Bunseki Kagaku, 55: 757-763 (2006).

Zhu, "Development of Chelating Resin-Packed Minicolumn for Multielement Preconcentration and Determination of Trace Metals in Natural Water," Bunseki Kagaku, 56: 895-896 (2007).

Expansion of the resin applied with a capture function select element: Development of high-precision analysis of trace metals, Exploratory Research Grant-in-Aid for Scientific Research (2005-2006).

Mercury Analysis Manual from the Ministry of the Environment, Japan (2004).

Table of relation between chelating agent and coupling constant, Dojindo Laboratories.

Office Action issued in corresponding Chinese Patent Application No. 201210363753.X dated Dec. 23, 2015.

Hong et al., "Extraction, Recovery, and Biostability of EDTA for Remediation of Heavy Metal-Contaminated Soil," Journal of Soil Contamination, 8: 81-103 (1999).

Office Communication issued in corresponding European Patent Application No. 12185503.5 dated Apr. 21, 2016.

\* cited by examiner

METHOD OF RECOVERING HEAVY METAL AND REAGENT FOR RECOVERY OF HEAVY METAL FOR USE IN THE SAME

CROSS-REFERENCE TO RELATED APPLICATIONS

This application claims priority from Japanese Patent Application Nos. 2011-207905 and 2012-182467, filed on Sep. 22, 2011 and Aug. 21, 2012, respectively and U.S. Provisional Application Ser. No. 61/538,748 filed on Sep. 23, 2011, the entire subject matter of which is incorporated herein by reference in its entirety.

BACKGROUND OF THE INVENTION

The present invention relates to a method of recovering a heavy metal and a reagent for recovery of a heavy metal for use in the same.

It is known that heavy metals such as mercury, cadmium, and lead are accumulated in human bodies, resulting in adverse effects on health. Therefore, it is important to analyze heavy metals in biological samples such as urine and the like and samples of food and beverage such as water and the like.

In analysis of a heavy metal, generally, as a pretreatment, foreign substances are removed from a sample, and a heavy metal is separated from the resultant sample. Then, the separated heavy metal is analyzed. As the pretreatment, a solvent extraction is widely used. The solvent extraction is a method in which a heavy metal in a sample is extracted in an organic medium, utilizing the polarity of a chelating agent to be bound to the heavy metal, according to the difference between the distribution coefficient of the chelating agent to an aqueous medium and that to the organic medium. The heavy metal can be further concentrated by evaporating the organic medium after the extraction. As a specific example of the solvent extraction, a dithizone method using, as the chelating agent, 1,5-diphenyl-3-thiocarbazone (hereinafter, also referred to as "dithizone") that is insoluble in an aqueous medium under acidic conditions is defined in JIS, for example (see, Mercury Analysis Manual, Ministry of the Environment, March 2004, Japanese Patent No. 2969226). In the dithizone method, first, dithizone and a liquid sample such as urine are mixed under acidic conditions, and thus, in the mixture thus obtained, a complex between the dithizone and a heavy metal being in the liquid sample is formed. Subsequently, an organic medium such as carbon tetrachloride or chloroform is added to the mixture. Then, the complex is extracted in the organic medium because the distribution coefficient of the complex to the aqueous medium is different from that of the complex to the organic medium. Thereafter, this organic medium is recovered. Thus, the heavy metal is recovered as the complex from the liquid sample. When the organic medium is evaporated, the heavy metal can be further concentrated.

However, the inventors of the present invention found a problem in that the recovery rates vary among samples when heavy metals are recovered by such a method even though the samples are treated under the same conditions. The variation in recovery rate among samples could lead to insufficient reliability of results obtained by quantitatively determining recovered heavy metals.

BRIEF SUMMARY OF THE INVENTION

Hence, the present invention is intended to provide a method of recovering a heavy metal by which the variation in heavy metal recovery rate among samples is suppressed.

In order to achieve the aforementioned object, a method of recovering a heavy metal according to the present invention is a method of recovering a heavy metal, the method including the steps of: forming a complex between a heavy metal in a sample and a chelating agent capable of chelating with a heavy metal in a mixture prepared by mixing the sample and the chelating agent; and recovering the heavy metal in the sample by recovering the complex, wherein in the step of forming a complex, the complex is formed in the presence of a masking agent for a thiol group in the mixture.

A method of analyzing a heavy metal according to the present invention is a method of analyzing a heavy metal, the method including the steps of: recovering a heavy metal from a sample by the method of recovering a heavy metal according to the present invention; and analyzing the heavy metal.

A reagent for recovery of a heavy metal according to the present invention contains a chelating agent capable of chelating with a heavy metal; and a masking agent for a thiol group.

According to the present invention, the variation in recovery rate among samples can be suppressed by forming a complex between a heavy metal being in a sample and a chelating agent in the presence of a masking agent. Moreover, according to the present invention, it is possible to increase the recovery rates from samples with low recovery rates, for example. Therefore, it is possible to analyze a heavy metal with superior reliability. Thus, the present invention is really useful in clinical examinations of biological samples and environmental testing, for example.

DETAILED DESCRIPTION OF THE INVENTION

The inventors of the present invention conducted earnest studies in order to elucidate the cause of the variation in recovery rate among samples. As a result of the earnest studies, they found as follows. The variation in recovery rate is significant among samples from especially subjects receiving a detoxication therapy for excreting heavy metals accumulated in their biological bodies, and the recovery rates from the samples are low. The detoxication therapy is generally conducted by a method of administrating a chelating agent in order to excrete heavy metals from a biological body. As the chelating agent, meso-2,3-dimercapto succinic acid (DMSA) or the like is used, for example. Hence, the inventors assumed as follows. DMSA contains a thiol group, so that the thiol group of the DMSA from a sample competed with dithizone added later against a heavy metal being in the sample. The heavy metal being in the sample could not sufficiently form a complex with the dithizone. Thus the recovery rate was reduced. Therefore the inventors actually used a masking agent for a thiol group when a complex between a chelating agent such as dithizone and a heavy metal is formed. Then the variation in recovery rate among samples was suppressed, and the recovery rates from the samples were increased.

The present invention can be applied in not only the above-mentioned samples from subjects receiving the detoxication therapy, but also samples from healthy subjects. It is considered that since many thiol group-containing compounds such as cysteine as an amino acid and the like are present in the biological body and samples from food, environment, and the like, the same effect as the DMSA is exerted. This is read as follows. For the same reason as in the case of DMSA, the variation in recovery rate among samples, which could be caused by these thiol-containing compounds can be suppressed by using the masking agent. It is to be noted that the present invention, however, is not at all limited by these assumptions.

<Method of Recovering Heavy Metals>

The method of recovering a heavy metal (hereinafter merely referred to as the "heavy metal recovering method") according to the present invention is, as mentioned above, a method of recovering a heavy metal, the method including the steps of; forming a complex between a heavy metal being in a sample and a chelating agent capable of chelating with a heavy metal in a mixture prepared by mixing the sample and the chelating agent; and recovering the heavy metal being in the sample by recovering the complex, wherein in the step of forming a complex, the complex is formed in the presence of a masking agent for a thiol group in the mixture.

The present invention is characterized in that the complex between the heavy metal being in the sample and the chelating agent are formed in the mixture in the presence of the masking agent, and other configurations and conditions are not at all limited.

In the heavy metal recovering method according to the present invention, the heavy metal to be recovered is not particularly limited. Examples thereof include Bi (bismuth), Hg (mercury), Cd (cadmium), Pd (palladium), Zn (zinc), Tl (thallium), Ag (silver), and Pb (lead). The form of the heavy metal in the sample is not particularly limited and may be, for example, a single heavy metal, an alloy of heavy metals, or a heavy metal-containing compound. The heavy metal-containing compound may be, for example, a heavy metal-containing organic compound or a heavy metal-containing inorganic compound. In the case where the heavy metal is Hg, Hg may be, for example, organic mercury or inorganic mercury. In the heavy metal recovering method according to the present invention, the heavy metal to be recovered may be, for example, one kind or two or more kinds. In the heavy metal recovering method according to the present invention, two or more kinds of heavy metals can be recovered at the same time by the single recovering treatment, for example.

In the heavy metal recovering method according to the present invention, the sample is not particularly limited. Examples thereof include a biological sample, a sample from the environment, a chemical substance, and a pharmaceutical. Examples of the chemical substance include reagents, pesticides, and cosmetics. The sample from the biological body is not particularly limited, and examples thereof include urine, blood, hair, and umbilical cords. Examples of the blood sample include erythrocytes, whole blood, sera, and plasma. Among them, a urine sample is preferred. The sample from the environment is not particularly limited, and examples thereof include an organism, food, water, the ground, and atmosphere and air. Examples of the organism include animals such as fish and shellfish and plants. Examples of the food sample include a fresh food and a processed food. Examples of the water sample include drinking water, groundwater, river water, seawater, and domestic sewage.

A fluid sample (liquid sample) is preferred as the sample because it can be handled easily, for example. An undiluted liquid or a diluted liquid obtained by suspending, dispersing, or dissolving the sample in a medium may be used as the liquid sample, for example. In the case where the sample is a solid, a diluted liquid obtained by suspending, dispersing, or dissolving the solid in a medium may be used as the liquid sample, for example. Hereinafter, the medium is referred to as a dilution medium. The dilution medium is not particularly limited, and examples thereof include water and a buffer solution. The buffer solution is not particularly limited, and examples thereof include a tris buffer solution, a phosphate buffer solution, an acetate buffer solution, a borate buffer solution, a citrate buffer solution, a veronal buffer solution, and various Good buffer solutions. The concentration of the buffer solution is not particularly limited and is, for example, from 10 to 100 mmol/l.

In the present invention, "masking" means inactivating the reactivity of a SH group and can be performed by chemically modifying a SH group, for example. The masking agent is not particularly limited, and a conventionally known masking agent can be used, for example. The masking agent includes an SH inhibitor. The chemical modification is not particularly limited, and examples thereof include alkylation, addition to an activated double bond, allylation, an exchange reaction with disulfide, oxidation, cyanidation, and mercaptide formation.

As the masking agent, a compound represented by at least one selected from the group consisting of the following structural formulae (1) to (3) can be used, for example. The compounds represented by the following structural formulae (1) to (3) may be used alone or in the combination of two or more of them, for example.

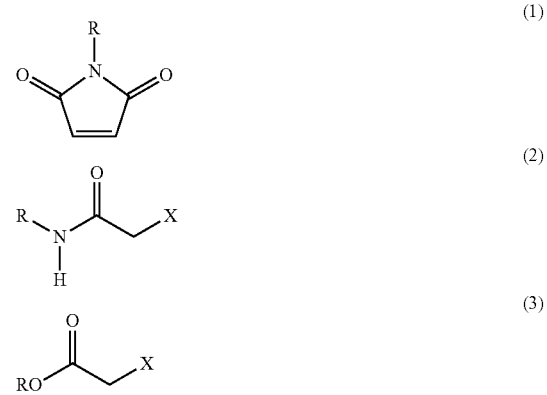

In the structural formula (1), R represents hydrogen, an alkyl group, a phenyl group, or a benzyl group. In the structural formula (2), R represents hydrogen, an alkyl group, a phenyl group, or a benzyl group, and X represents a halogen. In the structural formula (3), R represents hydrogen, an alkyl group, a phenyl group, or a benzyl group, and X represents a halogen.

The alkyl group is not particularly limited, and examples thereof include straight-chain or branched alkyl groups and aromatic alkyl groups. The carbon number of the alkyl group is, for example, from 1 to 7, preferably from 1 to 6, more preferably from 1 to 2, and still more preferably 2. Examples of the straight-chain or branched alkyl groups include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a n-hexyl group, an isohexyl group, a n-heptyl group, a n-octyl group, a n-nonyl group, and a n-decyl group. Any hydrogen in the alkyl group may be substituted, for example.

Any hydrogen in the phenyl group and the benzyl group may be substituted or unsubstituted, for example. Examples of the halogen include fluorine, chlorine, bromine, and iodine.

Examples of the masking agent represented by the structural formula (1) include maleimide, N-methylmaleimide, N-ethylmaleimide, N-phenylmaleimide, and maleimidepropionic acid, and N-ethylmaleimide is preferred. The compounds represented by the structural formula (1) may be used alone or in the combination of two or more of them, for example.

Examples of the masking agent represented by the structural formula (2) include halogenated acetamides such as iodoacetamide and the like, and iodoacetamide is preferred. The compounds represented by the structural formula (2) may be used alone or in the combination of two or more of them, for example.

Examples of the masking agent represented by the structural formula (3) include halogenated acetic acids such as iodoacetic acid and the like, and iodoacetic acid is preferred. The compounds represented by the structural formula (3) may be used alone or in the combination of two or more of them, for example.

In the heavy metal recovering method according to the present invention, the chelating agent preferably contains a sulfur-containing group, for example. The sulfur-containing group is a functional group containing a sulfur atom. The sulfur-containing group preferably is, for example, a thioketone group. The thioketone group is not particularly limited, and examples thereof include a thiocarbazone group, a thiosemicarbazone group, a thiocarbadiazone group, a thiourea group, a thiosemicarbazide group, and a rubeamate group.

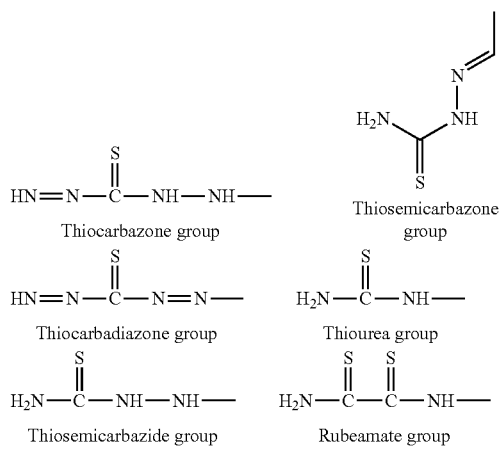

The chelating agent is, for example, preferably represented by the following structural formula (4).

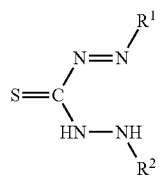

(4)

In the structural formula (4), $R^1$ and $R^2$ each represents a phenyl group. That is, the chelating agent represented by the structural formula (4) contains a thiocarbazone group and is 1,5-diphenyl-3-thiocarbazone (dithizone). The chelating agent of the structural formula (4) may be, for example, a salt.

Any hydrogen in the phenyl group may be substituted, for example. The hydrogen may be substituted with a halogen or an alkali metal such as sodium or potassium when substituted.

In the heavy metal recovering method according to the present invention, the chelating agent preferably contains a sulfur-containing group as mentioned above. The sulfur-containing group can be, for example, a thioketone group. The chelating agent containing a thioketone group can be, for example, a chelating agent containing at least one selected from the group consisting of a thiocarbazone group, a thiosemicarbazone group, a thiocarbadiazone group, a thiourea group, a thiosemicarbazide group, and a rubeamate group. Specific examples of the chelating agent include the following. These are mere examples, and the present invention is not at all limited by these examples.

(a1) Chelating agent containing a thiocarbazone group
e.g., 1,5-di(2-naphtyl)thiocarbazone (a2) Chelating agent containing a thiosemicarbazone group
e.g., acetone thiosemicarbazone, acetophenone thiosemicarbazone (a3) Chelating agent containing a thiocarbadiazone group
e.g., diphenylthiocarbadiazone (a4) Chelating agent containing a thiourea group
e.g., 1-acetyl-2-thiourea, guanyl thiourea, 1,3-bis(dimethylaminopropyl)-2-thiourea, tetramethyl thiourea, N,N'-diethyl thiourea, N,N'-diisopropyl thiourea, N,N'-dibutyl thiourea, 1,3-bis(dimethylaminopropyl)-2-thiourea, N-allyl-N'-(2-hydroxyethyl)thiourea, N,N'-bis(2-hydroxyethyl)thiourea, diacetyl thiourea, phenyl thiourea, N,N'-diphenyl thiourea, mono-o-tolyl thiourea, N,N'-di-o-tolyl thiourea, benzoyl thiourea (a5) Chelating agent containing a thiosemicarbazide group
e.g., phenylthiosemicarbazide, 4-phenylthiosemicarbazide, 4-methylthiosemicarbazide, thiosemicarbazide (a6) Chelating agent containing a rubeamate group
e.g., dithiooxamide (rubeanic acid)

In the step of forming a complex, the adding order of the sample, the chelating agent, and the masking agent is not particularly limited. Specifically, for example, the masking agent is added to the sample, and thereafter the chelating agent is further added, or the masking agent and the chelating agent are added to the sample at the same time.

The concentration of the sample in the mixture is not particularly limited and is, for example, in the range from 0.1 to 100 µg/l. It is preferred that the concentration of the undiluted sample in the mixture is in the above-described range.

The concentration of the masking agent in the mixture is not particularly limited and is, for example, in the range from 5 to 30 mg/ml, preferably from 10 to 20 mg/ml.

The mixing ratio between the masking agent and the sample in the mixture is not particularly limited and is, for example, in the range from 5 to 30 mg of the masking agent, preferably from 10 to 20 mg of the masking agent, per 1 ml of the sample.

The concentration of the chelating agent in the mixture is not particularly limited and is, for example, in the range from 0.1 to 0.3 mg/ml.

The mixing ratio between the chelating agent and the sample in the mixture is not particularly limited and is, for example, preferably in the range from 0.1 to 0.3 mg of the chelating agent per 1 ml of the sample.

The step of recovering the heavy metal is not particularly limited as long as the complex is recovered in the step. The heavy metal may be recovered as the complex or a single heavy metal by releasing it from the recovered complex, for example.

The heavy metal recovering method according to the present invention is described below with reference to embodiments. The present invention, however, is not limited by these embodiments.

(1) First Embodiment

The method according to the first embodiment is an example of recovering a heavy metal in an aqueous solvent using a chelating agent represented by the structural formula (4).

In the method according to the present embodiment, the step of forming a complex includes the following step (1A), and the step of recovering the heavy metal includes the following steps (1B) and (1C).

(1A) a step of forming a complex between a heavy metal being in a sample and a chelating agent in the presence of a masking agent in a mixture prepared by mixing the sample and the chelating agent under pH conditions where the chelating agent is insoluble in an aqueous solvent (1B) a step of recovering the complex from the mixture (1C) a step of dissolving the recovered complex in an aqueous medium under alkaline conditions in order to recover a heavy metal According to the present embodiment, a heavy metal can be recovered easily utilizing the difference in solubility of the chelating agent in an aqueous medium caused by the difference in pH conditions of the aqueous medium without substantially using an organic medium. Moreover, according to the present embodiment, the heavy metal recovery rate and heavy metal concentration rate can be increased.

(1A) Step of Forming Complex

In the step of forming a complex, a mixture of a sample and a chelating agent is prepared under pH conditions where the chelating agent can be insoluble in an aqueous solvent, and a complex between the heavy metal being in the sample and the chelating agent is formed in the mixture in the presence of a masking agent. Hereinafter, "the pH conditions where the chelating agent can be insoluble in an aqueous medium" are also referred to as the "pH conditions for insolubilization".

The chelating agent can maintain the state of being undissolved in the mixture under the pH conditions for insolubilization. Therefore, when a heavy metal is present in the sample, a complex between the chelating agent and the heavy metal being in the sample is formed in the mixture. The chelating agent is, for example, preferably in the state of being completely undissolved in the mixture and, however, may be in the state of being partially dissolved in the mixture. In the latter case, for example, it is only necessary that the amount of the remaining chelating agent being present in the mixture in the state of being undissolved therein is the amount capable of forming a complex with the heavy metal even in the case where the chelating agent is partially dissolved in the mixture.

In the step of forming a complex, the pH conditions for insolubilization are not particularly limited. The pH conditions for insolubilization can be, for example, acidic conditions (pH 5 or less), neutral conditions (pH 6 to 7), and alkaline conditions (more than pH 7 to pH 8 or less). The upper limit thereof is, for example, pH 8, preferably pH 6.8, more preferably pH 4, still more preferably pH 3, and particularly preferably pH 2. There is no particular limitation on the lower limit thereof, and the lower limit is preferably pH 1, for example. The pH conditions for insolubilization can be set as appropriate according to the kinds of the chelating agent to be used, for example.

It is only necessary for the mixture containing the chelating agent and the sample to be substantially an aqueous medium. The aqueous medium is a non-organic medium, means a so-called aqueous liquid. "Substantially an aqueous medium" means that it may be an aqueous medium containing trace amounts of an organic medium, for example.

The form of the chelating agent at the time of mixing with the sample is not particularly limited, and the chelating agent may be in the dry state (also referred to as the solid state) or in the liquid state, for example. In the latter case, the chelating agent is preferably a chelating agent-dispersion liquid obtained by dispersing the chelating agent in a non-organic medium in which the chelating agent cannot be dissolved. Hereinafter, the non-organic medium in which the chelating agent is dispersed is referred to as a "dispersion medium". The dispersion medium is, for example, a non-organic medium (aqueous medium) under the pH conditions for insolubilization. In the case where the pH conditions for insolubilization are acidic conditions, examples of the dispersion medium include an acid, an acid aqueous solution, and a buffer solution under the acidic conditions. In the case where the pH conditions for insolubilization are alkaline conditions, examples of the dispersion medium include an alkali, an alkali aqueous solution, and a buffer solution under the alkaline conditions. In the case where the pH conditions for insolubilization are neutral conditions, examples of the dispersion medium include, in addition to water, a neutral aqueous solution, and a buffer solution under the neutral conditions, the acid, the acid aqueous solution, the buffer solution under the acidic conditions, the alkali, the alkali aqueous solution, and the buffer solution under the alkaline conditions.

The acid is not particularly limited, and examples thereof include hydrochloric acid, sulfuric acid, acetic acid, boric acid, phosphoric acid, and citric acid. The acid aqueous solution can be, for example, one obtained by diluting an acid with water or a buffer solution. The buffer solution for use in the dilution of the acid is not particularly limited, and any of the above-mentioned general buffer solutions can be used. The concentration of the acid in the acid aqueous solution is not particularly limited and is, for example, more than 0N to 1N or less, preferably from 0.01N to 0.1N. The buffer solution under acidic conditions is not particularly limited, and examples thereof include a citrate buffer solution, an acetate buffer solution, a phosphate buffer solution, and Good buffer solutions. The concentration of the buffer solution under acidic conditions is not particularly limited and is, for example, from 10 to 100 mmol/l.

The neutral aqueous solution is not particularly limited, and examples thereof include a physiological saline solution, a phosphate buffer solution, and a tris buffer solution. The buffer solution under neutral conditions is not particularly limited. The concentration of the buffer solution under neutral conditions is not particularly limited and is, for example, from 10 to 100 mmol/l.

The alkali is not particularly limited, and examples thereof include sodium hydroxide and potassium hydroxide. The alkali aqueous solution can be, for example, one obtained by diluting an alkali with water or a buffer solution. The buffer solution for use in the dilution of the alkali is not particularly limited, and any of the above-mentioned general buffer solutions can be used. The concentration of the alkali in the alkali aqueous solution is not particularly limited and is, for example, more than 0N to $7 \times 10^{-3}$N or less. The buffer solution under alkaline conditions is not particularly limited, and examples thereof include Tris-NaOH, Tris-HCl, a carbonate buffer solution, and Good buffer solutions. The concentration of the buffer solution under alkaline conditions is not particularly limited and is, for example, from 10 to 100 mmol/l.

A method of mixing the sample and the chelating agent is not particularly limited. Examples of the method include the following methods (x) to (z):

(x) a method in which the sample whose conditions have been previously adjusted to the pH conditions for insolubilization and the chelating agent are mixed;

(y) a method in which the chelating agent whose conditions have been previously adjusted to the pH conditions for insolubilization and the sample are mixed; and (z) a method in which non-organic medium under the pH conditions for insolubilization or, the chelating agent, and the sample are mixed.

In the methods (x) to (z), the masking agent can be previously mixed with any of the chelating agent, the sample, and a non-organic medium, for example. The masking agent may be mixed in any of the sample and the chelating agent, before adjusting the conditions thereof to the pH conditions for insolubilization, for example. The masking agent may be mixed in any of the sample and the chelating agent, after adjusting the conditions thereof to the pH conditions for insolubilization, for example.

In the method (x), for example, the mixture under the pH conditions for insolubilization can be prepared by mixing the sample whose conditions have been adjusted to the pH conditions for insolubilization and the chelating agent, and thus the complex can be formed in the mixture. At that time, for example, the pH of the sample is adjusted so that the mixture prepared by mixing the chelating agent and the sample becomes under the pH conditions for insolubilization.

In the case where the pH conditions for insolubilization are acidic conditions, a method of adjusting the conditions of the sample to the acidic conditions is not particularly limited, for example. The adjustment can be performed by adding an acidic regent to the sample, for example. Examples of the acidic reagent include an acid, an acid aqueous solution, and a buffer solution under the acidic conditions. The acid is not particularly limited, and examples thereof include hydrochloric acid, sulfuric acid, citric acid, boric acid, phosphoric acid, and acetic acid. The acid aqueous solution can be, for example, one obtained by diluting an acid with water or a buffer solution. The buffer solution for use in the dilution of the acid is not particularly limited, and any of the above-mentioned general buffer solutions can be used. The concentration of the acid in the acid aqueous solution is not particularly limited and is, for example, from 0.01N to 5N. The buffer solution under the acidic conditions is not particularly limited, and examples thereof include a citrate buffer solution, an acetate buffer solution, a phosphate buffer solution, and Good buffer solutions. The concentration of the buffer solution under the acidic conditions is not particularly limited and is, for example, from 10 to 100 mmol/l.

In the case where the pH conditions for insolubilization are alkaline conditions, a method of adjusting the conditions of the sample to the alkaline conditions is not particularly limited, for example. The adjustment can be performed by adding an alkaline reagent to the sample, for example. Examples of the alkaline regent include an alkali, an alkali aqueous solution, and a buffer solution under the alkaline conditions such as mentioned above.

In the case where the pH conditions for insolubilization are neutral conditions, a method of adjusting the conditions of the sample to the neutral conditions is not particularly limited, for example. The adjustment can be performed by adding the acidic reagent, the alkaline reagent, or a neutral reagent to the sample according to the original pH conditions of the sample, for example. Examples of the neutral reagent include water, a neutral aqueous solution, and a buffer solution under the neutral conditions such as mentioned above.

In the method (y), for example, the mixture under the pH conditions for insolubilization can be prepared by mixing the sample and the chelating agent whose conditions have been adjusted to the pH conditions for insolubilization, and thus the complex can be formed in the mixture. At that time, for example, the pH of the chelating agent is adjusted so that the mixture prepared by mixing the sample and the chelating agent is under the pH conditions for insolubilization.

A method of adjusting the conditions of the chelating agent to the pH conditions for insolubilization is not particularly limited. Specifically, by dispersing the chelating agent in the dry state in a non-organic medium in which the chelating agent cannot be dissolved, the chelating agent-dispersion liquid whose conditions have been adjusted to the pH conditions for insolubilization can be obtained. As the non-organic medium in which the chelating agent is dispersed, any of the above-mentioned dispersion media such as the acidic reagent, the alkaline regent, and the neutral reagent can be used, for example.

The chelating agent in the dry state is superior in dispersibility in a non-organic medium, for example. Therefore, a dried chelating agent obtained by freeze-drying or drying under reduced pressure is preferred. A method of producing the dried chelating agent is not particularly limited, and for example, the dried chelating agent is obtained by mixing a chelating agent into an organic medium, and thereafter freeze-drying the mixture or drying the mixture under reduced pressure. The organic medium is not particularly limited, and for example, t-butyl alcohol or 2-propanol can be used.

In the method (z), for example, the mixture under the pH conditions for insolubilization can be prepared by mixing the non-organic medium under the pH conditions for insolubilization, the chelating agent, and the sample, and thus the complex can be formed in the mixture. At that time, for example, the pH of the non-organic medium is adjusted so that the mixture prepared by mixing the chelating agent, the sample, and the non-organic medium is under the pH conditions for insolubilization.

As the non-organic medium under the pH conditions for insolubilization, the acidic reagent, the alkaline reagent, the neutral reagent, or the like such as mentioned above can be used, for example.

A method of mixing the chelating agent and the sample is not particularly limited, and examples thereof include conventional methods such as mixing by repeatedly turning upside down, mixing by vibrating, and mixing by ultrasonic wave.

The mixture may contain any other component besides the chelating agent, the sample, and the masking agent. The any other component is not particularly limited, and examples thereof include an oxidizing agent and a reducing agent. The oxidizing agent can be used for improving reactivity of a reaction for forming a complex between the chelating agent and the heavy metal, for example. The reducing agent can be used for canceling the excess amount of the oxidizing agent when the mixture contains the excess amount of the oxidizing agent, for example.

The treatment conditions for forming the complex are not particularly limited, and the treatment temperature is, for example, room temperature, and the treatment time is, for example, from 30 seconds to 10 minutes.

(1B) Step of Recovering Complex

In the step of recovering the complex, the complex formed in the step of forming a complex is recovered from the mixture.

As mentioned above, the chelating agent can maintain the state of being undissolved in the mixture under the pH conditions for insolubilization. Therefore, the complex between the chelating agent and the heavy metal is present in the mixture in the state of being undissolved therein. Thus, in this step of recovering the complex, the undissolved complex being present in the mixture is recovered. The masking agent is present in a liquid fraction of the mixture and thus can be removed by the step of recovering the complex.

A method of recovering the complex is not particularly limited, and a conventionally known method of separating a solid from a liquid can be employed, for example. Examples of the method include centrifugal separation treatment, filtration treatment, precipitation treatment, membrane separation treatment, adsorption treatment, and freeze-drying treatment. The treatment conditions for recovering the complex are not particularly limited and can be set as appropriate according to the kind or amount of the complex, for example. In the case where the complex is recovered by the centrifugal separation treatment, the treatment conditions can be, for example, the centrifugal acceleration in the range from 19,600 to 29,400 m/s$^2$ (2,000 to 3,000×g), the temperature in the range from 4° C. to room temperature, and the time in the range from 1 to 10 minutes. The complex can be recovered by removing a supernatant after the centrifugal separation, for example. In the case where the complex is recovered by the filtration treatment, a filter to be used is not particularly limited, for example, and examples thereof include a filter paper, filter powder, and a membrane filter. After the filtration treatment, a fraction that has not passed through the filter can be recovered as the complex.

(1C) Step of Dissolving Complex

In the step of dissolving the complex, the heavy metal is recovered by dissolving the recovered complex in an aqueous medium under alkaline conditions.

The chelating agent is dissolved under alkaline conditions. Therefore, by mixing the recovered complex into an aqueous medium under alkaline conditions, the chelating agent in the state of being the complex can be dissolved in the aqueous medium. The aqueous medium in which the complex has been dissolved is also referred to as a complex aqueous solution. It is preferred that the complex is completely dissolved in the aqueous solution, for example, and however, the complex may partially remain in the state of being undissolved in the aqueous solution. It is preferred that the amount of the undissolved complex is the detection limit or less, for example.

There is no particular limitation on the alkaline conditions in the step of dissolving the complex. The lower limit of the alkaline conditions is, for example, preferably pH 9, more preferably pH 11. The upper limit of the alkaline conditions is not particularly limited and is, for example, preferably pH 12. The alkaline conditions can be set as appropriate according to the kind of the chelating agent to be used, for example. In the case where the pH conditions for insolubilization in the step of forming a complex are alkaline conditions, the alkaline conditions in the step of dissolving the complex preferably are at a pH higher than the former.

A method of dissolving the complex is not particularly limited. For example, the complex may be dissolved by adding the aqueous medium whose conditions have been previously adjusted to the alkaline conditions to the complex or by adding the complex to the aqueous medium and thereafter adjusting the conditions of the mixture thus obtained to alkaline conditions.

A method of adjusting the conditions to alkaline conditions is not particularly limited. For the adjustment, an alkaline reagent can be used, for example. Examples of the alkaline reagent include an alkali, an alkali aqueous solution, and a buffer solution under alkaline conditions. The alkali is not particularly limited, and examples thereof include sodium hydroxide and potassium hydroxide. The alkali aqueous solution can be, for example, one obtained by diluting an alkali with water or a buffer solution. The buffer solution for use in the dilution of the alkali is not particularly limited, and any of the above-mentioned general buffer solutions can be used. The concentration of the alkali in the alkali aqueous solution is not particularly limited and is, for example, from 0.1N to 1N. The buffer solution under alkaline conditions is not particularly limited, and examples thereof include Tris-NaOH, Tris-HCl, a carbonate buffer solution, and Good buffer solutions. The concentration of the buffer solution under alkaline conditions is not particularly limited and is, for example, from 10 to 100 mmol/l.

A method of mixing the complex and the aqueous medium is not particularly limited, and examples thereof include conventional methods such as mixing by repeatedly turning upside down, mixing by vibrating, and mixing by ultrasound.

The amount of the aqueous medium to be added to the complex is not particularly limited and is, for example, preferably the amount in which the recovered complex can be dissolved. The amount of the aqueous medium to be added is, for example, preferably less than the fluid amount of the sample. With this amount, a heavy metal-containing liquid with the heavy metal concentration higher than the sample can be obtained, for example. That is, a heavy metal-containing liquid in which the heavy metal is concentrated as compared with the sample can be obtained. The amount of the aqueous medium to be added with respect to the fluid amount of the sample is, for example, in the range from 1/2 to 1/100, preferably from 1/10 to 1/50, and more preferably 1/50.

In the present embodiment, the step of recovering the heavy metal may further include the step of decomposing the chelating agent being in the complex after dissolving the complex in an aqueous medium. By decomposing the chelating agent, a single heavy metal can be recovered from the complex. A method of decomposing the chelating agent is not particularly limited and can be, for example, a conventionally known method such as ashing. Examples of the ashing include wet ashing and dry ashing. The wet ashing can be performed according to the Mercury Analysis Manual (Ministry of the Environment, March 2004), for example.

The present embodiment is described below with reference to, as an example, a method of recovering mercury as a heavy metal, using acidic conditions as the pH conditions for insolubilization, dithizone as the chelating agent, and an urine sample as the sample. This, however, is a mere example, and the present invention is by no means limited thereto.

First, a sample mixture is prepared by adding the masking agent to the urine sample.

The amount of the urine sample is not particularly limited and is, for example, in the range from 1 to 100 ml, preferably from 1 to 20 ml, more preferably from 5 to 10 ml. The masking agent is added so as to have the above-mentioned concentration per 1 ml of the urine sample, for example.

The sample mixture may be stood for a predetermined time, for example. The treatment temperature is, for example, room temperature. The treatment time is, for example, from 30 seconds to 10 minutes.

Then, the pH of the sample mixture is adjusted to acidic conditions by adding the acidic reagent thereto. The amount of the acidic reagent to be added is not particularly limited and is, for example, in the range from 1 to 10 μl per 1 ml of the urine sample. The acidic reagent is, for example, preferably a hydrochloric acid aqueous solution, and the normality thereof is, for example, in the range from 1N to 8N.

Freeze-dried dithizone is placed in a tube, and thereafter the sample mixture whose pH has been adjusted is added thereto. The amount of the dithizone is, for example, from 0.1 to 0.3 mg, preferably 0.3 mg per 1 ml of the urine sample. At that time, the pH of the mixture after adding the dithizone is, for example, from, 1 to 4, preferably 1 to 2.

The prepared mixture is stood for a predetermined time, so that a complex between the dithizone and mercury being in the urine sample is formed. The treatment temperature is, for example, room temperature, and the treatment time is, for example, from 30 seconds to 10 minutes.

Then, the mixture is subjected to centrifugal separation, so that the mixture is separated into a precipitate containing the complex and a supernatant. Thereafter, the supernatant is removed, and an alkaline reagent is added to the tube containing the complex, so that the complex is dissolved in the alkaline reagent.

The amount of the alkaline reagent to be added is not particularly limited and is, for example, in the range from 10 to 200 μl, preferably from 20 to 100 μl, more preferably 20 μl, per 1 ml of the urine sample. The pH of the alkaline reagent is, for example, from 9 to 12, preferably from 11 to 12. The alkaline reagent is, for example, preferably a sodium hydroxide aqueous solution, and the normality thereof is, for example, in the range from 0.1N to 1N, preferably 0.4N.

As described above, mercury in the state of being a complex, being dissolved in the aqueous solution, can be recovered. Only mercury can be recovered by decomposing the dithizone in the complex by wet ashing, for example. An example of recovering mercury is described above. The present invention, however, is by no means limited thereto.

(2) Second Embodiment

The method according to the second embodiment is an example of recovering a heavy metal by an aqueous medium using chelating agents represented by the structural formulae (4) and (5). The second embodiment can be described with reference to the description of the first embodiment unless otherwise shown.

In the present embodiment, the chelating agent represented by the structural formula (4) is referred to as a first chelating agent, and the chelating agent represented by the structural formula (5) is referred to as a second chelating agent.

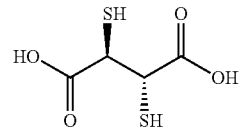

(5)

The second chelating agent represented by the structural formula (5) is meso-2,3-dimercapto succinic acid (DMSA). Hereinafter, the second chelating agent is also referred to as DMSA.

In the method according to the present embodiment, the step of forming a complex includes the following step (2A), and the step of recovering the heavy metal includes the following steps (2B) to (2D).

(2A) a step of forming a first complex between a first chelating agent and a heavy metal being in a sample in a first mixture prepared by mixing the sample and the first chelating agent in the presence of a masking agent, i.e., a step of preparing the first mixture under pH conditions where the first chelating agent can be insoluble in an aqueous medium (2B) a step of recovering a first complex from the first mixture (2C) a step of forming a second complex between the heavy metal from the first complex and a second chelating agent in a second mixture prepared by mixing the first complex and an aqueous solution of the second chelating agent (hereinafter also referred to as the "second chelating agent aqueous solution") in which the second chelating agent aqueous solution is under the pH conditions where the first chelating agent can be insoluble therein (2D) a step of recovering the second complex as a heavy metal by recovering, from the second mixture, a liquid fraction containing the second complex dissolved therein.

(2A) Step of Forming First Complex

A step of forming a first complex is a step of forming a first complex between a first chelating agent and a heavy metal being in a sample in a first mixture prepared by mixing the first chelating agent and the sample in the presence of a masking agent. In the step of forming a first complex, the first mixture is prepared under the pH conditions where the first chelating agent can be insoluble in an aqueous medium. Hereinafter, the "pH conditions where the first chelating agent can be insoluble in an aqueous medium" are also referred to as the "first pH conditions". The first pH conditions are the "pH conditions for insolubilization" in the first embodiment and can be described with reference to the description of the first embodiment.

The step of forming a first complex (2A) is the step (1A) of the first embodiment and can be described with reference to the description of the first embodiment.

(2B) Step of Recovering First Complex

In the step of recovering the first complex, the first complex formed in the step of forming a first complex is recovered from the first mixture.

The step of recovering the first complex (2B) is the step (1B) of the first embodiment and can be described with reference to the description of the first embodiment.

(2C) Step of Forming Second Complex

A step of forming a second complex is a step of forming a second complex between the heavy metal from the first complex and a second chelating agent in a second mixture prepared by mixing the first complex and a second chelating agent aqueous solution. In the step of forming a second complex, the second chelating agent aqueous solution is under the pH conditions where the first chelating agent can be insoluble therein. Hereinafter, the "pH conditions where the first chelating agent can be insoluble in the second chelating agent aqueous solution" are also referred to as the "second pH conditions".

The second chelating agent is in the state of being dissolved in the second mixture, and the first complex can maintain the state of being undissolved in the same. Then, when the first complex and the second chelating agent are present in the second mixture, the heavy metal forming the first complex is completely or partially dissociated from the first complex and binds to the second chelating agent, so that a second complex between the second chelating agent and the heavy metal is formed, although the mechanism is unknown.

The second pH conditions are, for example, pH conditions where the second chelating agent can be soluble in an aqueous medium, and the first complex can be insoluble in the same. In the step of forming a second complex, the pH conditions of the second chelating agent aqueous solution and the pH conditions of the second mixture of the aqueous solution and the first complex are both preferably the second pH conditions.

The second pH conditions can be, for example, non-alkaline conditions, and specific examples thereof include acidic conditions (pH 2 to 3), mildly acidic conditions (pH 4 to 5), and neutral conditions (pH 6 to 7). The upper limit of the second pH conditions is not particularly limited and is, for example, pH 6.8, preferably pH 6, more preferably pH 4. The lower limit of the second pH conditions is not particularly limited and is, for example, pH 2, preferably pH 3, more preferably pH 4. The second pH conditions can be set as appropriate according to the kinds of the first chelating agent and the second chelating agent, for example.

It is only necessary for the second chelating agent aqueous solution to be obtained by dissolving the second chelating agent in an aqueous medium, for example. The second chelating agent is, for example, preferably in the state of being completely dissolved in the aqueous solution and, however, may be in the state of being partially dissolved in the aqueous solution. In the latter case, for example, it is only necessary that the amount of the remaining second chelating agent being present in the aqueous solution is the amount capable of forming a second complex with the heavy metal from the first complex, for example.

The second chelating agent aqueous solutions may be prepared by adjusting the pH of an aqueous medium to the second pH conditions and thereafter dissolving the second chelating agent therein or adding the second chelating agent to an aqueous solution and thereafter adjusting the pH of this second mixture thus obtained to the second pH conditions, for example.

In the former case, since DMSA as the second chelating agent is a strong acid, the aqueous medium in which the second chelating agent is dissolved is, for example, preferably an alkaline reagent. By dissolving the second chelating agent in the alkaline reagent, the aqueous solution under the second pH conditions, preferably under non-alkaline conditions, can be prepared. The pH of the alkaline reagent is not particularly limited, the lower limit thereof is, for example, 8, preferably 9, more preferably 10, and the upper limit thereof is, for example, 12, preferably 11. The alkaline reagent is not particularly limited and is, for example, preferably an alkaline aqueous solution, more preferably an alkaline buffer solution. The alkaline aqueous solution can be, for example, a trisodium phosphate aqueous solution. Examples of the alkaline buffer solution include a phosphate buffer solution, a tris buffer solution, and Good buffer solutions. The concentrations of the alkaline aqueous solution and the alkaline buffer solution are not particularly limited and are, for example, from 10 to 100 mmol/l, preferably 100 mmol/l.

In the latter case, the aqueous medium is not particularly limited, and for example, water, an aqueous solution, a buffer solution, or the like can be used. For example, the aqueous medium and the second chelating agent are mixed, and thereafter, the conditions of the second mixture thus obtained are adjusted to the second pH conditions. A method of adjusting the conditions of the second mixture is not particularly limited, and in the method, the acidic reagent, the alkaline reagent, and the neutral reagent can be used as appropriate, for example.

The concentration of the second chelating agent in the second chelating agent aqueous solution is not particularly limited and is, for example, from 5 to 20 mg/ml, preferably from 10 to 20 mg/ml.

A method of mixing the first complex and the second chelating agent aqueous solution is not particularly limited, and examples thereof include conventional methods such as mixing by repeatedly turning upside down, mixing by vibrating, and mixing by ultrasound.

The amount of the second chelating agent aqueous solution to be added in the second mixture is not particularly limited. The amount is, for example, preferably from 10 to 200 µl, more preferably from 20 to 100 µl, yet more preferably 20 µl, per 1 ml of the sample used in the step of forming a first complex. The ratio between the first complex and the second chelating agent to be added in the second mixture is not particularly limited. The ratio (ratio by weight) between the first chelating agent used in the step of forming a first complex and the second chelating agent used in the step of forming a second complex is, for example, from 1:0.3 to 1:40, preferably from 1:7 to 1:40, more preferably from 1:10 to 1:40.

The amount of the second chelating agent aqueous solution to be added to the first complex is not particularly limited and is, for example, preferably less than the fluid amount of the used sample. With this amount, a heavy metal-containing liquid with a heavy metal concentration higher than that of the used sample can be obtained, for example. That is, a heavy metal-containing liquid in which a heavy metal is concentrated as compared with the sample can be obtained. The amount of the second chelating agent aqueous solution to be added is, for example, in the range from 1/2 to 1/100, preferably from 1/10 to 1/50, more preferably 1/50.

The second mixture may further contain any other component besides the first complex and the second chelating agent aqueous solution. The any other component is not particularly limited, and examples thereof include the oxidizing agent and the reducing agent such as mentioned above.

The treatment conditions for forming a second complex are not particularly limited, and the treatment temperature is, for example, room temperature, and the treatment time is, for example, from 30 seconds to 10 minutes.

(2D) Step of Recovering Second Complex

In the step of recovering the second complex, the heavy metal is recovered by recovering, from the second mixture, a liquid fraction containing the second complex formed in the step of forming a second complex, dissolved therein.

As mentioned above, the second chelating agent is in the state of being dissolved in the second mixture under the second pH conditions. Therefore, the second complex between the second chelating agent and the heavy metal is also present in the state of being dissolved in the second mixture. On the other hand, the first chelating agent is in the state where it can be insoluble in the second mixture. Therefore the first chelating agent is present in the state of being undissolved in the second mixture. Thus, the heavy metal is recovered by recovering a liquid fraction containing the second complex dissolved therein in this step of recovering the second complex. The second complex is, for example, preferably in the state of being completely dissolved in the second mixture, and however, may be in the state of being partially undissolved in the second mixture. It is preferred that the amount of the undissolved second complex is the detection limit or less, for example.

A method of recovering the liquid fraction is not particularly limited, and a conventionally known method of separating a solid from a liquid can be employed, for example. The method can be described with reference to the example of the method of recovering the liquid fraction in the step (1B) of the first embodiment, for example. For example, in the case of filtration treatment using a filter, a fraction passed through the filter by the filtration treatment can be recovered as the liquid fraction.

In the present embodiment, the step of recovering the heavy metal may further include the step of decomposing the second chelating agent in the second complex after recovering the liquid fraction. By decomposing the second chelating agent, a single metal can be recovered from the second complex. A method of decomposing the second chelating agent is not particularly limited, and examples thereof include conventionally known methods such as ashing and the like. The method of decomposing the second chelating agent can be described with reference to the description of the first embodiment.

The present embodiment is described below with reference to, as an example, a method of recovering mercury as a heavy metal using acidic conditions as the first pH conditions, mildly acidic conditions to neutral conditions as the second pH conditions, dithizone as the first chelating agent, DMSA as the second chelating agent, and an urine sample as the sample. This, however, is a mere example, and the present invention is not limited thereby.

In the same manner as in the first embodiment, a masking agent is added to a urine sample, the pH of the sample mixture thus obtained is then adjusted, thereafter dithizone is added thereto. Thus, a complex between the dithizone and mercury in the sample is formed.

Then, in the same manner as in the first embodiment, a first mixture thus obtained is subjected to centrifugal separation. Thus, the first mixture is separated into a precipitate containing the first complex and a supernatant. The supernatant is removed, and a DMSA aqueous solution is added to the first complex being in the tube. Thus, a second complex is formed in a second mixture of the first complex and the DMSA aqueous solution.

The DMSA aqueous solution can be prepared by dissolving DMSA in an alkaline aqueous solution, for example. The alkaline aqueous solution is, for example, preferably a trisodium phosphate aqueous solution, and the concentration thereof is, for example, from 10 to 100 mmol/l, and the pH thereof is, for example, from 9 to 12. The concentration of DMSA in the DMSA aqueous solution is, for example, from 5 to 20 mg/ml. The pH of the DMSA aqueous solution is, for example, in the range from 2 to 6, preferably in the range from 4 to 6, more preferably 4.

The amount of the DMSA aqueous solution to be added to the first complex is not particularly limited and is, for example, in the range from 10 to 200 μl, preferably 20 to 100 μl, more preferably 20 μl per 1 ml of the urine sample. The pH of the second mixture of the first complex and the DMSA aqueous solution is, for example, in the range from 2 to 6, preferably from 4 to 6, more preferably 4.

Then, the second mixture is subjected to centrifugal separation, so that the second mixture is separated into a supernatant containing the second complex dissolved therein and a precipitate. Thereafter, the supernatant is recovered.

As described above, mercury in the state of being the second complex, being dissolved in the liquid fraction can be recovered. Only mercury can be recovered by decomposing the DMSA in the second complex by wet ashing, for example. An example of recovering mercury is described above, and the present invention, however, is by no means limited thereto.

(3) Third Embodiment

The third embodiment is an example of recovering a heavy metal by an aqueous medium using a chelating agent represented by the following structural formula (6) as a second chelating agent. The present embodiment can be described with reference to the description on the second embodiment unless otherwise shown.

In the structural formula (6), $R^3$ represents an alkyl group or an aminoalkyl group with a carbon number of 1 or 2 or is not present, and Y represents,

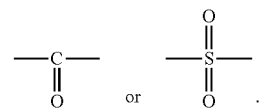

Examples of the second chelating agent include thiopronine (N-(2-mercaptopropionyl)glycine) represented by the following structural formula (6-1), DMPS (1,2-dimercapto-1-propanesulfonic acid sodium salt) represented by the following structural formula (6-2), and cysteine (2-amino-3-sulfanylpropionic acid) represented by the following structural formula (6-3). The second chelating agent may be, for example, any of hydrates of compounds having the structural formula (6). The second chelating agent may be, for example, any of tautomers and streoisomers thereof. Examples of the isomers include geometric isomers, conformers, and the like. As the second chelating agent, any of commercially available products may be used, for example. The thiopronine is available from KANTO CHEMICAL CO., INC., Tokyo Chemical Industry Co., Ltd., Wako Pure Chemical Industries, Ltd., or the like, for example. The DMPS is available from Wako Pure Chemical Industries, Ltd. or the like, for example. The cysteine is available from any of various companies including NACALAI TESQUE, INC. and the like, for example. The second chelating agent may be used alone or in a combination of two or more of them.

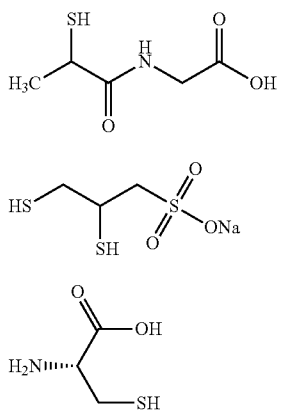

The heavy metal recovering method according to the present embodiment can be described with reference to the description of the second embodiment except that the second chelating agent represented by the structural formula (6) is used, unless otherwise shown. Specifically, the method can be carried out by the steps (2A) to (2D).

In the step of forming a second complex (2C), a second mixture of the first complex and a second chelating agent aqueous solution is prepared, and thus a second complex between a heavy metal from the first complex and the second chelating agent is formed in the second mixture.

In the step (2C), the second pH conditions are, for example, the pH conditions where the second chelating agent can be soluble in an aqueous medium, and the first complex can be insoluble in the same. In the step of forming a second complex, the pH conditions of the second chelating agent aqueous solution and the pH conditions of the second mixture of the aqueous solution and the first complex preferably are the second pH conditions. The pH of the second mixture may be any pH as long as the first chelating agent is not dissolved therein.

The second pH conditions can be, for example, non-alkaline conditions, and specific examples thereof include acidic conditions (pH 1 to 3), mildly acidic conditions (pH 4 to 5), and neutral conditions (pH 6 to 7). The upper limit of the second pH conditions is not particularly limited and is, for example, pH 6.8, preferably pH 6, more preferably pH 4. The lower limit of the second pH conditions is not particularly limited and is, for example, pH 4, preferably pH 3, more preferably pH 2, yet more preferably pH 1. The second pH conditions can be set as appropriate according to the kinds of the first chelating agent, the second chelating agent, and the like, for example It is only necessary for the second chelating agent aqueous solution to be obtained by dissolving the second chelating agent in an aqueous medium, for example. The second chelating agent is, for example, preferably in the state of being completely dissolved in the aqueous solution and, however, may be in the state of being partially dissolved in the aqueous solution. In the latter case, for example, it is only necessary that the amount of the remaining second chelating agent being present in the aqueous solution is the amount capable of forming a second complex with the metal from the first complex, for example.

The second chelating agent aqueous solution may be prepared by adjusting the pH of an aqueous medium to the second pH conditions and thereafter dissolving the second chelating agent therein or adding the second chelating agent to an aqueous medium and thereafter adjusting the pH of this mixture thus obtained to the second pH conditions, for example.

In the former case, the aqueous medium in which the second chelating agent is dissolved is not particularly limited, and for example, water, an aqueous solution, a buffer solution, or the like can be used. For example, the pH of the aqueous medium is adjusted to the second pH conditions, and thereafter the second chelating agent is dissolved therein. A method of adjusting the pH of the aqueous medium is not particularly limited, and in the method, an acidic reagent, an alkaline reagent, and a neutral reagent can be used as appropriate, for example.

In the latter case, the aqueous medium is not particularly limited, and for example, water, an aqueous solution, a buffer solution, or the like can be used. For example, the aqueous medium and the second chelating agent are mixed, and thereafter, the pH of the mixture thus obtained is adjusted to the second pH conditions. A method of adjusting the pH of the mixture is not particularly limited, and in the method, the acidic reagent, the alkaline reagent, and the neutral reagent can be used as appropriate, for example.

The concentration of the second chelating agent in the second chelating agent aqueous solution is not particularly limited and is, for example, from 15 to 300 mg/ml, preferably from 75 to 150 mg/ml. In the present embodiment, the second chelating agent preferably is thiopronine, DMPS, or cysteine because of having superior solubility. For example, as the concentration of the second chelating agent in the second chelating agent aqueous solution is increased, the amount of the formed second complex between the heavy metal from the first complex and the second chelating agent can be increased. Thus, the heavy metal recovery rate can be increased.

The present embodiment is described below with reference to, as an example, a method of recovering a mercury as a heavy metal using acidic conditions as the first pH conditions, mildly acidic conditions to neutral conditions as the second pH conditions, dithizone as the first chelating agent, DMPS as the second chelating agent, and an urine sample as the sample. This, however, is a mere example, and the present invention is not limited thereby.

In the same manner as in the first embodiment, a masking agent is added to a urine sample, the pH of the sample mixture thus obtained is then adjusted, and thereafter dithizone is added thereto. Thus, a complex between the dithizone and mercury being in the sample is formed.

Then, in the same manner as in the first embodiment, a first mixture thus obtained is subjected to centrifugal separation. Thus, the first mixture is separated into a precipitate containing the first complex and a supernatant. The supernatant is removed, and a DMSA aqueous solution is added to the first complex being in the tube. Thus, a second complex is formed in a second mixture of the first complex and the DMSA aqueous solution.

The DMPS aqueous solution can be prepared by dissolving DMPS in a medium, for example. Examples of the medium include a trisodium phosphate aqueous solution, nitric acid, acetic acid, phosphoric acid, citric acid, a phosphate buffer solution, and a tris buffer solution. The concentration of the DMPS aqueous solution is, for example, from 10 to 100 mmol/l. The pH of the medium is not particularly limited as long as dithizone is not dissolved. The concentration of DMPS in the DMPS aqueous solution is, for example, from 5 to 20 mg/ml. The pH of the DMPS aqueous solution is, for example, in the range from 2 to 6, preferably from 4 to 6, more preferably 4.

The amount of the DMPS aqueous solution to be added to the first complex is not particularly limited and is, for example, in the range from 10 to 200 μl, preferably from 20 to 100 μl, more preferably 20 μl per 1 ml of the urine sample. The pH of the second mixture of the first complex and the DMPS aqueous solution is, for example, in the range from 2 to 6, preferably from 1 to 3, more preferably 1.

Then, the second mixture is subjected to centrifugal separation, so that the second mixture was separated into a supernatant containing the second complex dissolved therein and a precipitate. Thereafter, the supernatant is recovered.

As described above, mercury dissolved in a liquid fraction in the state of being the second complex can be recovered. Only mercury can be recovered by decomposing the second chelating agent in the second complex by wet ashing, for example. An example of recovering mercury is described above, and the present invention, however, is by no means limited thereto. Moreover, in the present embodiment, DMPS is used as a second chelating agent. A heavy metal can be recovered in the same manner as in the present embodiment even in the case of using thiopronine, cysteine, or the like as a second chelating agent, for example.

(4) Another Embodiment

In the heavy metal recovering method according to the present invention, examples of the step of recovering the heavy metal include a method of extracting the complex with an organic medium in addition to the heavy metal recovering method using an aqueous medium according to the embodiments. In this case, for example, the step of recovering a heavy metal may be carried out according to the dithizone method (colorimetric method) and the atomic absorption method, defined in JIS K0101 and JIS K0102, respectively.

<Method of Analyzing Heavy Metal>

The method of analyzing a heavy metal (hereinafter merely referred to as the "heavy metal analyzing method") according to the present invention is, as mentioned above, a method of analyzing a heavy metal, the method including the steps of; recovering a heavy metal from a sample by the heavy metal recovering method according to the present invention; and analyzing the heavy metal. The step of recovering a heavy metal can be described with reference to the description of the heavy metal recovering method according to the present invention.

The step of analyzing the heavy metal is not particularly limited and can be selected as appropriate according to the kind of the heavy metal to be analyzed, for example. The analysis of the heavy metal can be performed by, for example, an optical measurement, GC-ECD (gas chromatography-electron capture detector), an electrochemical measurement (e.g., stripping voltammetry), or the like. The analysis by the optical measurement can be performed by measuring an absorbance, a transmittance, a reflectance, or the like using an optical analyzer, for example. Examples of the optical analyzer include an atomic absorption spectrometer and a visible spectrometer. The analysis of the heavy metal may be qualitative analysis or quantitative analysis, for example.

The heavy metal analyzing method according to the present invention may further include the step of correcting a measurement value, for example. In the step of correcting a measurement value, a measurement value as a measurement result can be corrected according to the correlation between the measurement value and the heavy metal concentration in a sample, for example. The correlation can be obtained as follows, for example. A heavy metal in the standard samples with the known heavy metal concentrations is recovered by the heavy metal recovering method according to the present invention, and measurement values of the heavy metal and the corresponding heavy metal concentrations are plotted. It is preferred that the standard samples are in a dilution series. By correcting measurement values as described above, it becomes possible to perform the quantitative determination with higher reliability.

The heavy metal may be analyzed as the above mentioned complex or as a single heavy metal obtained by isolating the heavy metal from the complex, for example. In the latter case, it is preferred that the step of recovering the heavy metal includes the step of decomposing the chelating agent being in the complex, i.e., the step of isolating the heavy metal from the complex as mentioned above.

<Reagent for Recovery of Heavy Metal>

The reagent for recovery of a heavy metal (hereinafter merely referred to as the "heavy metal recovery reagent") according to the present invention is, as mentioned above, a reagent for recovery of a heavy metal, for use in the heavy metal recovering method according to the present invention, the reagent comprising: a chelating agent capable of chelating with a heavy metal; and a masking agent for a thiol group. The heavy metal recovery reagent according to the present invention is characterized in that it contains the chelating agent and the masking agent, and the other configuration and conditions are not particularly limited. The chelating agent and the masking agent can be described with reference to the description of the heavy metal recovering method according to the present invention, for example.

<Kit for Recovery of Heavy Metal>

A kit for recovery of a heavy metal (hereinafter merely referred to as the "heavy metal recovery kit") according to the present invention is a kit for recovery of a heavy metal, for use in the heavy metal recovering method according to the present invention, the kit including: a chelating agent capable of chelating with a heavy metal; and a masking agent for a thiol group. The heavy metal recovery kit according to the present invention is characterized in that it includes: the chelating agent; and the masking agent, and the other configuration and conditions are not particularly limited. The chelating agent and the masking agent can be described with reference to the description of the heavy metal recovering method according to the present invention, for example. The chelating agent and the masking agent may be stored in different containers or stored in the same container in the mixed state or unmixed state, for example.

The heavy metal recovery kit may further contain any other reagent in addition to the chelating agent and the masking agent, for example. The any other reagent is not particularly limited, and examples thereof include an oxidizing agent, a reducing agent, and the like.

<Method of Pretreating Sample>

The method of pretreating a sample (hereinafter merely referred to as the "sample pretreating method") according to the present invention is a method of pretreating a sample, applied in the heavy metal recovering method according to the present invention, the method including: adding a masking agent for a thiol group to a sample prior to forming a complex between a heavy metal being in the sample and a chelating agent capable of chelating with a heavy metal. The sample pretreating method according to the present invention can be described with reference to the description of the heavy metal recovering method according to the present invention.

The heavy metal analyzing method according to the present invention can be, for example, a second method of analyzing a heavy metal (hereinafter referred to as a "second heavy metal analyzing method") described below other than the above-mentioned aspect. The second heavy metal analyzing method according to the present invention is a method of analyzing a heavy metal, the method including the steps of: forming a complex between a heavy metal being in a sample and a chelating agent capable of chelating with a heavy metal in a mixture prepared by mixing the sample and the chelating agent; and analyzing the heavy metal by detecting the complex, wherein in the step of forming a complex, the complex is formed in the mixture in the presence of a masking agent for a thiol group.

As the chelating agent, a chelating agent which can be detected in the state of forming a complex with a heavy metal and cannot be detected in the state of not forming a complex with a heavy metal can be used, for example. According to this chelating agent, a heavy metal composing the complex can be detected indirectly by detecting the complex regardless of where or not the complex is recovered, for example. The second heavy metal analyzing method according to the present invention does not need to include the step of recovering the heavy metal by recovering the complex, for example.

In the second heavy metal analyzing method according to the present invention, the chelating agent can be, for example, the above-mentioned dithizone. A method of detecting a complex between the dithizone and the heavy metal is not particularly limited, and a conventionally known method can be employed. The complex can be detected by a measurement of optical signal such as absorbance. The step of forming a complex in the second heavy metal analyzing method can be fully described with reference to the above description.

A second method of pretreating a sample according to the present invention is a method of pretreating a sample, applied in the second heavy metal analyzing method according to the present invention, the method including: adding a masking agent for a thiol group to a sample prior to forming a complex between a heavy metal being in the sample and a chelating agent capable of chelating with a heavy metal.

EXAMPLES

Next, the examples of the present invention are described. The present invention, however, is not limited by the following examples.

Example 1

(1) Sample Preparation

Urine samples (n=3) were collected from a healthy subject, and mercury chloride (II) was then added thereto so as to each have a concentration of 10 μg/l. Thus, samples A were obtained. Urine samples (n=3) were collected from subjects into which meso-2,3-dimercapto succinic acid (DMSA) had been administrated once as a therapy for removing a heavy metal from the body. The urine samples were used as samples B, C, and D.

(2) Chelating Agent Preparation 1.5 mg of dithizone (produced by Fluka) was dissolved in 1 ml of t-butyl alcohol (NACALAI TESQUE, INC.). The whole amount of this solution thus obtained was introduced into a 15 ml-capacity conical tube made of polypropylene (PP) (Produced by Nunc), which was then subjected to freeze-drying.

(3) Recovery of Mercury from Sample

N-ethylmaleimide (NEM) as a masking agent was dissolved in 5 ml of each sample A to D so as to have a concentration of 0, 12.5, or 25 mmol/l. The solution thus obtained was then stood still for 15 minutes at room temperature. Thus, thiol group-containing compounds contained in the sample were masked with the NEM. 5N hydrochloric acid (produced by NACALAI TESQUE, INC.) was added to the sample after the addition of NEM, so that the pH thereof was adjusted to about 1 to 2.

The whole amount of the sample after the pH adjustment was added to the tube containing the dithizone, which was then shaken for 5 minutes at room temperature so as to mix the sample and the dithizone. Thus, a complex between the dithizone and mercury was formed. Thereafter, the tube was subjected to centrifugal separation (19,600 m/s$^2$ (2000×g), 20° C., 10 minutes). Thus, the mixture was separated into a precipitate containing the complex and a supernatant.

The supernatant was subjected to wet ashing, so that organic substances were decomposed. The wet ashing was performed according to the Mercury Analysis Manual (Ministry of the Environment, March 2004). Then, the mercury amount contained in the supernatant was determined by an atomic absorption spectrometer (MERCURY ANALYZER™, produced by Nippon Instruments Co., Ltd.). The mercury amount (Y) in the sample obtained after the addition of dithizone was calculated by deducting the mercury amount contained in the supernatant from the mercury amount (X) in a sample before the addition of dithizone. The mercury amount (X) in the sample before the addition of dithizone is the mercury amount determined after wet ashing the sample obtained after the pH adjustment in the same manner as mentioned above without mixing dithizone thereinto.

$Y = X - $ mercury amount (ng) in supernatant

X: mercury amount (ng) in sample before addition of dithizone

Y: mercury amount (ng) in sample after addition of dithizone

Then, the mercury amount in the sample before the addition (adsorption) of dithizone and the mercury amount in the sample after the addition (adsorption) of dithizone were substituted into the following formula (1). Thus, the mercury recovery rate (%) was determined.

$$\text{Recovery rate (\%)} = 100 \times Y/X \qquad (1)$$

X: mercury amount (ng) in sample before addition of dithizone

Y: mercury amount (ng) in sample after addition of dithizone

The following Table 1 shows a relationship between the NEM concentration and the recovery rate in each of the samples. In Table 1, "before adsorption" indicates the known mercury amount in the sample before the addition of dithizone, and "after adsorption" indicates the mercury amount recovered from the sample after the addition of the dithizone. As shown in Table 1, when the NEM concentration was 0 mmol/l, the recovery rate from the sample A collected from a healthy subject was 85.53%, whereas the respective recovery rates of the samples B to D collected from the subjects into which DMSA had been administrated were 87.83%, 37.54%, and 69.50%. The recovery rates varied among the samples collected from the subjects into which DMSA had been administrated as a therapy for removing a heavy metal from the body. In contrast, the recovery rate was increased in proportion to the increase in the NEM concentration by subjecting the samples B to D to masking treatment by adding NEM thereto as a masking agent. The variation in recovery rate among the samples was extremely reduced. The recovery rates comparable to that of the sample A collected from a healthy subject could be obtained.

reagent 3 was added thereto. Then, the absorbances at the time of the addition (0 second) and at the time after 30 seconds from the addition were measured at the wavelength of 490 nm. The absorbance at the time of the addition (0 second) was deducted from the absorbance at the time after

TABLE 1

| | | NEM concentration (mmol/l) | | | | | | | | | | |
|---|---|---|---|---|---|---|---|---|---|---|---|---|
| | | Sample A | | | Sample B | | | Sample C | | | Sample D | |
| | | 0 | 12.5 | 25 | 0 | 12.5 | 25 | 0 | 12.5 | 25 | 0 | 12.5 | 25 |
| Mercury amount (ng) | before adsorption | 41.92 | — | — | 40.70 | 39.70 | 39.67 | 22.13 | 21.93 | 21.50 | 8.76 | 8.42 | 8.76 |
| | after adsorption | 35.02 | — | — | 35.74 | 34.25 | 36.97 | 8.31 | 18.36 | 19.12 | 6.09 | 6.92 | 7.55 |
| Recovery rate (%) | | 83.53 | — | — | 87.83 | 86.27 | 93.18 | 37.54 | 83.72 | 88.92 | 69.50 | 82.18 | 86.21 |

For example, the recovery rates vary among samples when mercury in samples containing thiol group-containing compounds such as DMSA and the like is recovered by forming complexes with dithizone. However, as described above, it was found that, according to the present invention, the variation in recovery rate among samples could be alleviated by treatment with a masking agent, and the mercury recovery rate could be increased.

Example 2

(1) Sample Preparation

A urine sample (n=1) collected from a healthy subject was used as a sample a. A sample obtained by adding DMSA to the sample a so as to have a concentration of 0.2 mmol/l was used as a sample b (n=1). A urine sample (n=1) collected from a subject into which DMSA had been administrated once was used as a sample c. The respective samples obtained by adding mercury chloride (II) (produced by Wako Pure Chemical Industries, Ltd.) to samples a to c so as to each have a concentration of 1 ppm were used as samples a1 to c1. Hereinafter, samples a to c are also referred to as samples without addition of mercury, and samples a1 to c1 are also referred to as samples with addition of mercury.

(2) Masking Agent Preparation

NEM was added to purified water so as to have a final concentration of 50 mmol/l. Thus, an NEM solution was prepared and was used as a masking agent 1.

(3) Colorimetric Reagent

A mixture was prepared by adding nitric acid and lauryl sodium sulfate to purified water. This was used as a colorimetric reagent 2. In the colorimetric reagent 2, the final concentration of the nitric acid was 0.13N, the final concentration of the lauryl sodium sulfate was 0.9%. A dithizone solution was prepared by dissolving dithizone in ethanol so as to have a final concentration of 0.024 mmol/l. This was used as a colorimetric reagent 3.

(4) Recovery of Mercury from Sample 0.49 ml each of 6 samples, namely samples a to c and a1 to c1, were dispensed in different containers. Then, 0.01 ml of the masking agent 1 was introduced into each container, which was then stood still for 15 minutes at room temperature. Thus, pretreatment using NEM was performed. Subsequently, 0.03 ml of the colorimetric reagent 2 was introduced into the container. Further, 0.02 ml of the colorimetric 30 seconds from the addition. This value thus obtained was used as a signal value of each of the samples a to c and a1 to c1.

The differences ($\Delta$) in signal value between the samples with addition of mercury (a1, b1, and c1) and the samples without addition of mercury (a, b, and c) were determined. Then, assuming that the difference ($\Delta$ a1−a) in signal value between the sample a1 with addition of mercury and the sample a without addition of mercury was 100%, the relative values (%) were calculated as the recovery rates.

As a comparative example, signal values, the differences ($\Delta$) in signal value, and the recovery rates were determined in the same manner as described above except that 0.01 ml of purified water was used as substitute for NEM as the masking agent 1.

The following Table 2 shows the results. As shown in Table 2, in the comparative example using purified water in pretreatment, the recovery rate with respect to the samples b and b1 to which DMSA was administrated and the recovery rate with respect to the samples c and c1 from a subject into which DMSA was administrated were significantly reduced compared with the recovery rate with respect to the samples a and a1 from a healthy subject to which DMSA was not added. In contrast, in the example using NEM in pretreatment, the recovery rate with respect to the samples b and b1 to which DMSA had been added and the recovery rate with respect to the samples c and c1 from a subject into which DMSA had been administrated were 75% or more which were superior.

TABLE 2

| | Pretreatment: purified water | | | Pretreatment: reagent 1 (NEM) | | |
|---|---|---|---|---|---|---|
| | Signal value | $\Delta$ | Recovery rate (%) | Signal value | $\Delta$ | Recovery rate (%) |
| Sample a | 0.149 | 0.150 | 100 | 0.144 | 0.151 | 100 |
| Sample a1 | 0.299 | | | 0.295 | | |
| Sample b | 0.146 | 0.044 | 29 | 0.149 | 0.135 | 90 |
| Sample b1 | 0.190 | | | 0.284 | | |
| Sample c | 0.156 | 0.043 | 28 | 0.153 | 0.114 | 75 |
| Sample c1 | 0.198 | | | 0.267 | | |

For example, in the case where thiol group-containing compounds such as DMSA and the like are contained in samples, the recovery rates vary among the samples when mercury is recovered as complexes with dithizone. However, as described above, according to the present invention, the variation in recovery rate among samples could be reduced by treatment with a masking agent.

Example 3

(1) Sample Preparation 0.2 mmol/l of DMSA was added to a urine sample collected from a healthy subject.

(2) Chelating Agent Preparation

A chelating agent of dithizone was prepared in the same manner as in Example 1.

(3) Recovery of Mercury from Sample

Mercury was recovered using the chelating agent, and the recovery rate was determined, in the same manner as in Example 1 except that iodoacetic acid or iodoacetamide as a masking agent was dissolved in 5 ml of the sample so as to have a concentration of 12.5 mmol/l. As a comparative example, mercury was recovered using the chelating agent, and the recovery rate was determined in the same manner as in Example 1 except that the sample was stood still for 15 minutes at room temperature without dissolving the masking agent therein.

The following Table 3 shows the results. As shown in Table 3, the recovery rate was increased in the case where iodoacetic acid or iodoacetamide as a masking agent was dissolved in the sample as compared with the comparative example using no masking agent.

TABLE 3

| | | Masking agent | | |
|---|---|---|---|---|
| | | None | Iodoacetic acid | Iodoacetamide |
| Mercury amount (ng) | before adsorption | 48.81 | 48.81 | 48.81 |
| | after adsorption | 21.67 | 49.19 | 49.20 |
| Recovery rate (%) | | 44.39 | 100.78 | 100.80 |

Example 4

(1) Sample Preparation

A urine sample was collected from a subject into which meso-2,3-dimercapto succinic acid (DMSA) had been administrated once as a therapy for removing a heavy metal from the body.

(2) Chelating Agent Preparation

A chelating agent using dithizone was prepared in the same manner as in Example 1.

(3) Recovery of Mercury from Sample

Mercury was recovered using the chelating agent, and the recovery rate was determined, in the same manner as in Example 1 except that NEM as a masking agent was dissolved in 5 ml of the sample so as to have a concentration of 12.5 mmol/l. As a comparative example, mercury was recovered using the chelating agent, and the recovery rate was determined, in the same manner as in Example 1 except that the sample was stood still for 15 minutes at room temperature without dissolving the masking agent therein.

The following Table 4 shows the results. As shown in Table 4, in the case where the NEM as a masking agent was dissolved in the sample, the recovery rate was increased as compared with the comparative example using no masking agent.

TABLE 4

| | | Masking agent | |
|---|---|---|---|
| | | None | NEM |
| Mercury amount (ng) | before adsorption | 60.22 | 60.22 |
| | after adsorption | 42.86 | 57.05 |
| Recovery rate (%) | | 71.17 | 94.73 |

Example 5

(1) Preparation of Sample and Chelating Agent

A sample and a chelating agent of dithizone were prepared in the same manner as in Example 4.

(2) Second Chelating Agent Preparation

Thiopronine (produced by KANTO CHEMICAL CO., INC.) was dissolved in 0.1 mol/l nitric acid aqueous solution so as to have a concentration of 500 mmol/l. Thus, a thiopronine aqueous solution was prepared as a second chelating agent.

(3) Recovery of Mercury from Sample

In the same manner as in Example 4, a complex was formed, and a supernatant was removed. The thiopronine aqueous solution as a second chelating agent was added to the whole amount of the precipitate being in the tube, which was then shaken for 5 minutes at room temperature so as to mix the complex and the aqueous solution as the second chelating agent. Thus, a complex (second complex) between mercury and the thiopronine was formed in the mixture thus obtained. The tube was subjected to centrifugal separation ($19,600$ m/s$^2$ ($2000 \times g$), 20° C., 10 minutes), so that the mixture was separated into a supernatant containing the second complex dissolved therein and a precipitate. The supernatant was recovered and used as a mercury-concentrated sample.

The mercury-concentrated sample was subjected to wet ashing, so that organic substances were decomposed. The wet ashing was performed according to the Mercury Analysis Manual (Ministry of the Environment, March 2004). The mercury concentration of the mercury-concentrated sample after the ashing was determined by an atomic absorption spectrometer (MERCURY ANALYZER™, produced by Nippon Instruments Co., Ltd.). Furthermore, the mercury concentration of the sample containing no chelating agent of dithizone, masking agent, and second chelating agent were determined by an atomic absorption spectrometer in the same manner as described above. As a comparative example, the mercury concentration was determined using the chelating agent of dithizone and the second chelating agent in the same manner as described above except that the sample was stood still for 15 minutes at room temperature without dissolving the masking agent thereinto.

The mercury concentration ($X_C$) and amount ($X_V$) of the mercury-concentrated sample and the mercury concentration ($Y_C$) and the amount ($Y_V$) of the sample were substituted into the following formula (2). Thus, the mercury recovery rate (%) was determined.

$$\text{Recovery rate (\%)} = 100 \times (X_C \times X_V)/(Y_C \times Y_V) \qquad (2)$$

The Table 5 shows the results. As shown in Table 5, in the case where the masking agent was dissolved in the sample, the recovery rate was increased as compared with the comparative example using no masking agent.

TABLE 5

|  |  | Masking agent | |
|---|---|---|---|
|  |  | None | NEM |
| Mercury concentration (µg/l) | before concentration | 12.04 | 12.04 |
|  | after concentration | 233.20 | 326.71 |
| Recovery rate (%) | | 38.72 | 54.25 |

Example 6

(1) Sample Preparation

A sample was prepared in the same manner as in Example 4.

(2) Chelating Agent Preparation 0.15 mg of dithizone (Produced by Fluka) was pounded in a mortar and used.

(3) Second Chelating Agent Preparation

A second chelating agent was prepared in the same manner as in Example 5.

(4) Recovery of Mercury from Sample

Each of NEM, maleimide, and N-methylmaleimide (NMM) as a masking agent was dissolved in 4 ml each of the sample so as to have a concentration of 12.5 mmol/l, which was then stood still for 15 minutes at room temperature. Thus, thiol group-containing compounds contained in the sample were masked with the masking agent.

The dithizone as a chelating agent was added to the sample, and a citric acid (anhydride) (produced by Kishida Chemical Co., Ltd.)/trisodium citrate dehydrate (produced by Wako Pure Chemical Industries, Ltd.) buffer agent was added thereto so as to have a final concentration of 100 mM. The first mixture thus obtained was then shaken for 20 minutes at room temperature so as to mix the sample and the dithizone. Thus, a first complex between the dithizone and mercury was formed. Thereafter, the whole amount of the first mixture of the sample and the dithizone was placed in a filter container provided with a filter paper made of glass fibers, which was then subjected to centrifugal filtration. Thus, the first mixture was separated into a precipitate containing the first complex and a filtrate.

The thiopronine aqueous solution as a second chelating agent was added to the precipitate, which was then stood still for 15 minutes at room temperature so as to mix the complex and the aqueous solution of the second chelating agent. Thus, a complex (second complex) between mercury and thiopronine was formed in the second mixture. The filter container was subjected to centrifugal filtration in the same manner as described above, and a filtrate containing the second complex dissolved therein was fractionated. The filtrate was recovered and used as a mercury-concentrated sample.

The mercury recovery rate was determined in the same manner as in Example 1 except that the mercury-concentrated sample was subjected to wet ashing. Further, the mercury concentration of the mercury-concentrated sample was determined by an atomic absorption spectrometer in the same manner as in Example 5. As a comparative example, the mercury recovery rate was determined using a chelating agent of dithizone and a second chelating agent, and the mercury recovery rate was determined, in the same manner as described above except that the sample was stood still for 15 minutes at room temperature without dissolving the masking agent therein.

The following Tables 6 and 7 show the results. As shown in Tables 6 and 7, in the case where the masking agent was dissolved in the sample, the recovery rates were increased as compared with the comparative example using no masking agent.

TABLE 6

|  |  | Masking agent | | | |
|---|---|---|---|---|---|
|  |  | None | NEM | Maleimide | NMM |
| Mercury amount (ng) | before adsorption | 39.04 | 39.04 | 39.04 | 39.04 |
|  | after adsorption | 25.05 | 34.61 | 33.23 | 34.73 |
| Recovery rate (%) | | 64.16 | 88.64 | 85.11 | 88.95 |

TABLE 7

|  |  | Masking agent | | | |
|---|---|---|---|---|---|
|  |  | None | NEM | Maleimide | NMM |
| Mercury concentration (µg/l) | before concentration | 9.76 | 9.76 | 9.76 | 9.76 |
|  | after concentration | 179.02 | 244.95 | 250.59 | 257.30 |
| Recovery rate (%) | | 18.34 | 25.10 | 25.68 | 26.36 |

Example 7

(1) Sample Preparation

Samples (6 samples, n=1) were collected from healthy subjects, and mercury chloride (II) was then added thereto so as to each have a concentration of 10 µg/l. Thus, samples A to F were obtained.

(2) Chelating Agent Preparation 0.04 mg of dithizone (Produced by Fluka) was pounded in a mortar and used.

(3) Recovery of Mercury from Sample

N-methylmaleimide (NMM) as a masking agent was dissolved in 1 ml each of samples A to F so as to have a concentration of 0 or 12.5 mmol/l. The whole amount of this solution thus obtained was introduced into a 15 ml-capacity conical tube made of polypropylene (PP) (Produced by Nunc), which was then stood still for 15 minutes at room temperature. Thus, thiol group-containing compounds contained in the sample were masked with the NMM. A citric acid/trisodium citrate buffer solution was added to each of the samples A to F after the addition of NMM so as to have a concentration of 100 mmol/l, so that each pH thereof was adjusted to about 2 to 3.

The dithizone was added to each sample after the pH adjustment, which was then shaken for 20 minutes at room temperature so as to mix the sample and the dithizone. Thus, a complex between dithizone and mercury was formed. Thereafter, the tube was subjected to centrifugal separation (186,200 m/s$^2$ (19000×g), 20° C., 5 minutes). Thus, the mixture was separated into a precipitate containing the complex and a supernatant.

In the same manner as in Example 1, the precipitate was subjected to wet ashing, and the mercury amount contained in the precipitate and the mercury recovery rate (%) were determined.

The following Table 8 shows a relationship between the NMM concentration and the mercury recovery rate. In Table 8, "before adsorption" indicates the known amount of mercury in the sample before the addition of dithizone, and "after adsorption" indicates the amount of mercury recovered from the sample by adding dithizone thereinto. As shown in Table 8, when the NMM concentration was 0 mmol/l, the respective recovery rates from the samples A to F were 85.05%, 72.37%, 83.35%, 67.94%, 87.05%, and 74.18%, and the recovery rates varied among the samples. In contrast, the recovery rates were increased by subjecting the samples A to F to masking treatment by adding NMM thereto as a masking agent, and the variation in recovery rate among the samples was reduced.

TABLE 8

| | | NMM concentration (mmol/l) | | | | | | | | | | | |
|---|---|---|---|---|---|---|---|---|---|---|---|---|---|
| | | Sample A | | Sample B | | Sample C | | Sample D | | Sample E | | Sample F | |
| | | 0 | 12.5 | 0 | 12.5 | 0 | 12.5 | 0 | 12.5 | 0 | 12.5 | 0 | 12.5 |
| Mercury amount (ng) | before adsorption | 10.35 | 10.35 | 10.74 | 10.74 | 10.45 | 10.45 | 10.74 | 10.74 | 9.91 | 9.91 | 10.83 | 10.83 |
| | after adsorption | 8.81 | 8.75 | 7.77 | 8.60 | 8.71 | 8.63 | 7.29 | 8.23 | 8.63 | 8.39 | 8.03 | 8.90 |
| Recovery rate (%) | | 85.05 | 84.5 | 72.37 | 80.10 | 83.35 | 82.58 | 67.94 | 76.69 | 87.05 | 84.69 | 74.18 | 82.15 |

For example, the recovery rates vary among samples when mercury in samples containing thiol group-containing compounds such as DMSA and the like is recovered by forming complexes with dithizone. However, as described above, it was found that, according to the present invention, the variation in recovery rate among samples could be alleviated by treatment with a masking agent, and the mercury recovery rate could be increased.

As described above, according to the present invention, the occurrence of variation in recovery rate among samples such as mentioned above can be suppressed by forming a complex between a heavy metal in a sample and a chelating agent in the presence of a masking agent. Moreover, according to the present invention, it is possible to increase the recovery rates from samples with low recovery rates, for example. Therefore, it is possible to perform analysis of a heavy metal with superior reliability. Thus, the present invention is really useful in clinical examinations of biological samples and environmental testing, for example.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A method of recovering a heavy metal from a sample, the method comprising the steps of:
   contacting a sample comprising a heavy metal with a sufficient amount of a thiol group masking agent to inactivate reactivity of thiol groups present in the sample;
   mixing a substantially aqueous dispersion of a chelating agent under pH conditions such that the chelating agent is insoluble in the aqueous dispersion and where the chelating agent comprises a thioketone group, with the sample to form a complex between the heavy metal and the chelating agent; and
   recovering the heavy metal by separating the complex from the sample.

2. The method according to claim 1, wherein the chelating agent and the masking agent are added to the sample in the complex-forming step.

3. The method according to claim 1, wherein the chelating agent is added to the sample after the addition of the masking agent.

4. The method according to claim 1, wherein the masking agent is at least one selected from the group consisting of the following structural formulae (1) to (3),

 (1)

 (2)

 (3)

wherein:
R is hydrogen, an alkyl group, a phenyl group, or a benzyl group and
X is a halogen.

5. The method according to claim 4, wherein
   the masking agent of the structural formula (1) is maleimide, N-methylmaleimide, or N-ethylmaleimide;
   the masking agent of the structural formula (2) is iodoacetamide; and
   the masking agent of the structural formula (3) is iodoacetic acid.

6. The method according to claim 1, wherein the chelating agent is 1,5-diphenyl-3-thiocarbazone.

7. The method according to claim 1, wherein the sample is a biological sample.

8. The method according to claim 1, wherein the heavy metal is at least one selected from the group consisting of Bi, Hg, Cd, Pd, Zn, Tl, Ag, and Pb.

9. A method of analyzing a heavy metal, the method comprising the steps of:
   recovering a heavy metal from a sample by the method according to claim 1; and
   analyzing the recovered heavy metal.

10. A method of pretreating a sample subject to the method according to claim 1, the method comprising: adding the masking agent to the sample prior to formation of the complex between the heavy metal and the chelating agent.

11. A reagent for recovery of a heavy metal present in a sample, comprising:
    a substantially aqueous dispersion of a chelating agent under pH conditions such that the chelating agent is insoluble in the aqueous dispersion and where the chelating agent comprises a thioketone group and is capable of chelating with a heavy metal; and
    a thiol group masking agent,
wherein the masking agent is at least one selected from the group consisting of the following structural formulae (1) to (3),

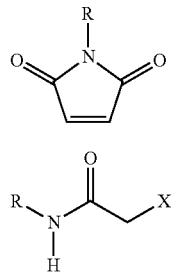

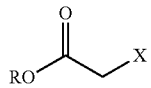

wherein:

R is hydrogen, an alkyl group, a phenyl group, or a benzyl group and

X is a halogen.

12. The reagent according to claim 11, wherein
    the masking reagent of the structural formula (1) is maleimide, N-methylmaleimide, or N-ethylmaleimide;
    the masking reagent of the structural formula (2) is iodoacetamide; and
    the masking reagent of the structural formula (3) is iodoacetic acid.

13. The reagent according to claim 11, wherein the chelating agent is 1,5-diphenyl-3-thiocarbazone.

* * * * *